US012656254B2

(12) United States Patent
Montoy

(10) Patent No.: US 12,656,254 B2
(45) Date of Patent: Jun. 16, 2026

(54) METHOD AND SYSTEM FOR CONTROLLING THE MANUFACTURE OF RUBBER PRODUCTS IN RESPONSE TO THE PHYSICOCHEMICAL PROPERTIES OF A RUBBER MIXTURE

(71) Applicant: COMPAGNIE GENERALE DES ETABLISSEMENTS MICHELIN, Clermont-Ferrand (FR)

(72) Inventor: Aurelien Montoy, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 47 days.

(21) Appl. No.: 18/710,475

(22) PCT Filed: Nov. 10, 2022

(86) PCT No.: PCT/EP2022/081479
§ 371 (c)(1),
(2) Date: May 15, 2024

(87) PCT Pub. No.: WO2023/088778
PCT Pub. Date: May 25, 2023

(65) Prior Publication Data
US 2025/0012719 A1     Jan. 9, 2025

(30) Foreign Application Priority Data
Nov. 16, 2021    (FR) ....................................... 2112099

(51) Int. Cl.
*G01N 21/552*        (2014.01)
*G01N 33/00*         (2006.01)

(52) U.S. Cl.
CPC ....... *G01N 21/553* (2013.01); *G01N 33/0034* (2013.01); *G01N 2201/04* (2013.01)

(58) Field of Classification Search
CPC ............. G01N 21/553; G01N 33/0034; G01N 2201/04; G01N 2021/8416; B29D 30/0061; B29D 2030/0066
See application file for complete search history.

(56) References Cited

U.S. PATENT DOCUMENTS 10,928,369 B2     2/2021  Herrier et al.
2018/0356388 A1*  12/2018  Shiba ................. G01N 33/2852
(Continued)

FOREIGN PATENT DOCUMENTS

FR      3063543 A1     9/2018
FR      3091346 A1     7/2020
(Continued)

OTHER PUBLICATIONS

Becher, C et al. "Detection of Evaporating Hazardous Material Released from Moving Sources Using a Gas Sensor Network." Sensors and actuators. B, Chemical 146.2 (2010): (Year: 2010).*
(Continued)

*Primary Examiner* — Georgia Y Epps
*Assistant Examiner* — Monica T Taba
(74) *Attorney, Agent, or Firm* — VENABLE LLP

(57)                ABSTRACT

A method (200) for controlling the manufacture of rubber products produced by a rubber-product manufacturing system (100) utilizes the output from an olfactory-profiles model as an identification of the physicochemical properties of the rubber mixture in the process of being produced in the production facility (110). A system (100) for manufacturing rubber products performs a method (200) for controlling the manufacture of rubber products, the system including a production facility (110) that implements successive mixing
(Continued)

steps, an odor detection device (120) that captures ambient air of the production facility in order to obtain at least one gas sample during the mixing cycle, and a control subsystem (130) that employs an olfactory-profiles model based on the physicochemical properties of the rubber mixtures recognized by surface plasmon resonance (SPR).

15 Claims, 4 Drawing Sheets

(56) References Cited

U.S. PATENT DOCUMENTS

| | | | |
|---|---|---|---|
| 2020/0088702 A1 | 3/2020 | Herrier et al. | |
| 2020/0256793 A1* | 8/2020 | Hou-Broutin | ........ G01N 33/007 |
| 2022/0120682 A1 | 4/2022 | Caritu et al. | |
| 2022/0203637 A1 | 6/2022 | Knapp et al. | |
| 2022/0252564 A1 | 8/2022 | Hou-Broutin et al. | |
| 2022/0341847 A1 | 10/2022 | Caritu et al. | |
| 2022/0390382 A1 | 12/2022 | Caritu et al. | |

FOREIGN PATENT DOCUMENTS

| | | |
|---|---|---|
| WO | 2021/009440 A1 | 1/2021 |
| WO | 2021/053284 A1 | 3/2021 |
| WO | 2021/053285 A1 | 3/2021 |
| WO | 2021/011397 A1 | 6/2021 |

OTHER PUBLICATIONS

International Search Report dated Feb. 9, 2023, in corresponding PCT/EP2022/081479 (4 pages).

N.H. Kamarulzaman, et al., "Quantification of VOCs and the Development of Odor Wheels for Rubber Processing", Science of the Total Environment 657, 154-168 (2019).

S. Brenet, et al., "Highly Selective Optoelectronic Nose Based on Surface Plasmon Resonance Imaging for Sensing Volatile Organic Compounds", Anal. Chem. 2018, 90, 9879-9887.

L. Bastien, "Artificial neural networks: what are they and what are they used for?", https://www.lebigdata.fr/reseau-de-neurones-artificiels-definition with English translation (retrieved Dec. 30, 2025).

* cited by examiner

[Fig. 1]
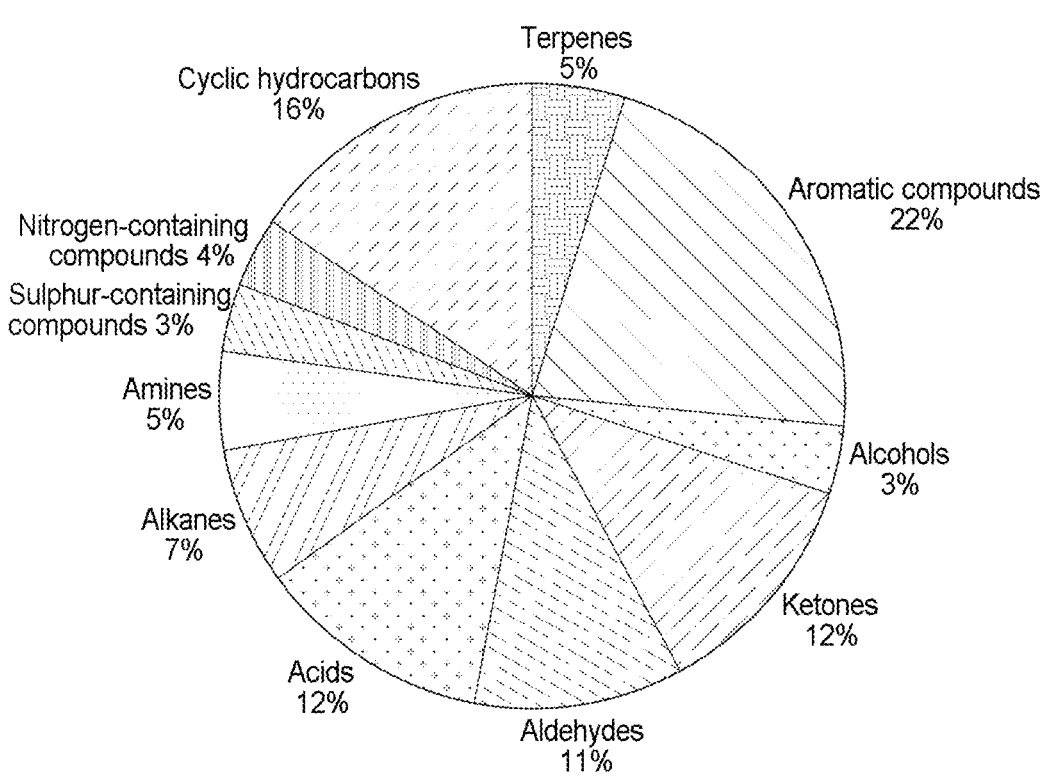

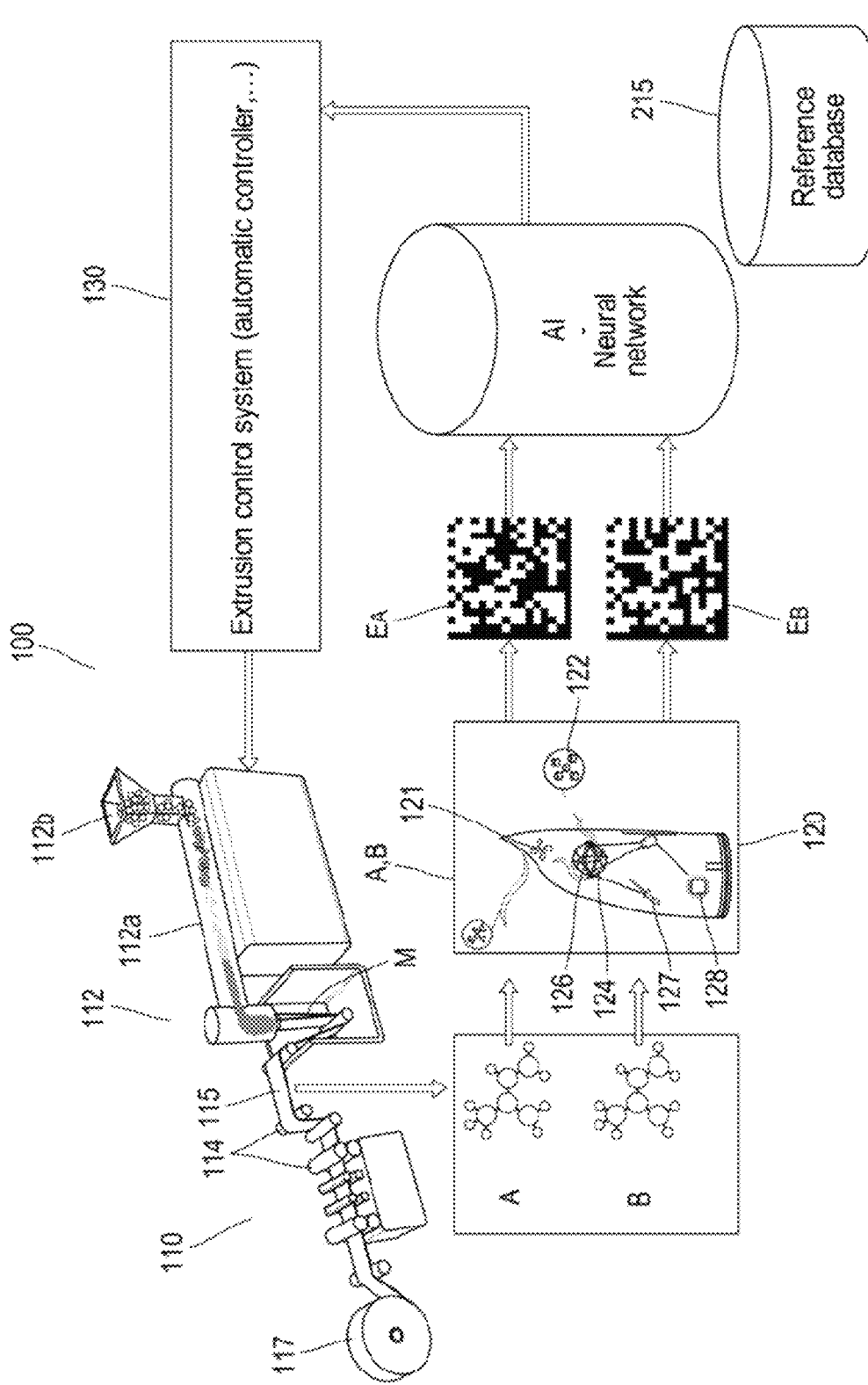
[Fig. 2]

[Fig. 3]
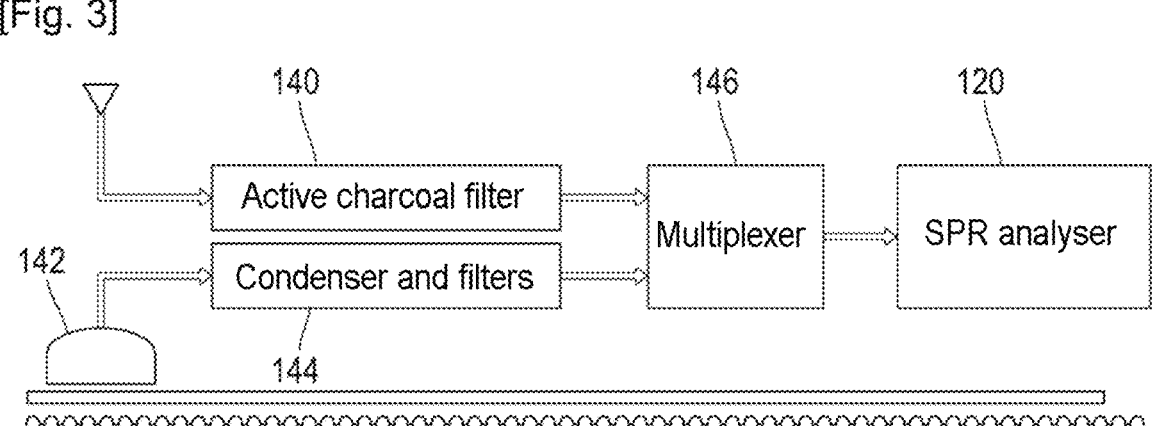

[Fig. 4]
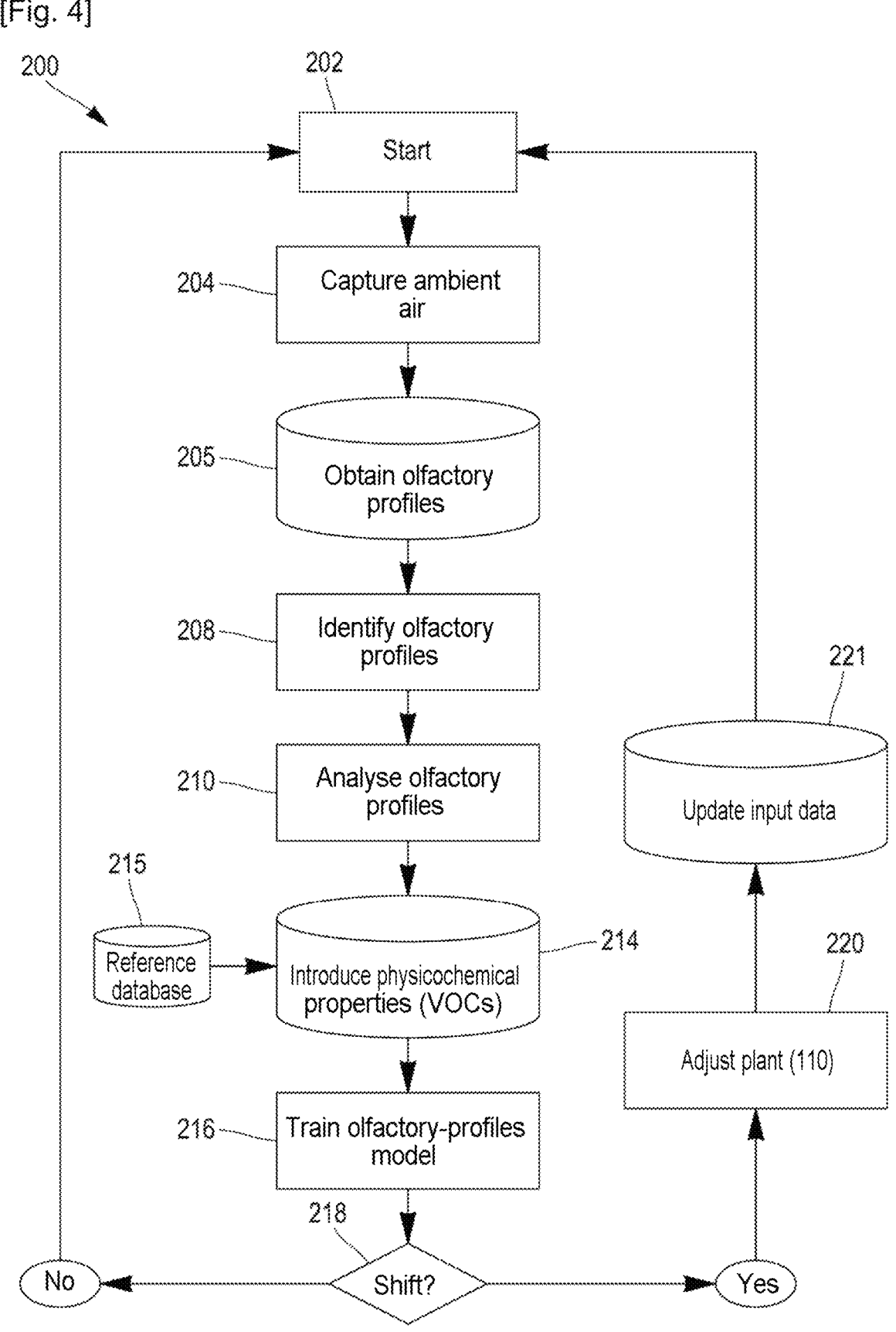

METHOD AND SYSTEM FOR CONTROLLING THE MANUFACTURE OF RUBBER PRODUCTS IN RESPONSE TO THE PHYSICOCHEMICAL PROPERTIES OF A RUBBER MIXTURE

TECHNICAL FIELD

The invention is directed to the use of substantially "olfactory" measurements in facilities where rubber products (including tires) are manufactured from rubber mixtures. More specifically, the invention is directed to systems and methods for determining correlations between one or more physical phenomena associated with a rubber (for example, its tack) and the changes to volatile organic mixtures originating from rubber mixtures.

BACKGROUND

The field of manufacture of rubber products (including tires) from rubber mixtures involves methods having numerous steps of converting the raw materials, including, without limitation, milling and washing steps, hot convection steps for drying wet rubber crumbs, the packaging of dried rubber and the storing of the manufactured rubber. Emissions of volatile organic compounds (or VOCs) from the various rubbers reveal a number of odorants, both in terms of odorant concentration and in terms of odorant type. During these methods, monitoring the VOCs offers a valuable opportunity to evaluate the changes in the composition of the VOCs emitted while the rubber is being processed.

In one study that compares the VOCs emitted directly from the raw materials of the rubber or of the unconverted rubber, the identified compounds were classified into various chemical groups (for example, acids, alcohols, aromatic mixtures, aldehydes, alkanes, ethers, esters, cyclic hydrocarbons, ketones, sulfurous compounds, nitrogen-containing compounds, terpenes, and others) (see "Quantification of VOCs and the Development of Odor Wheels for Rubber Processing", Nor H. Kamarulzaman, Nhat Le-Minh, Ruth M. Fisher, Richard M. Stuetz, *Science of the Total Environment* 657 (2019)) (the "Kamarulzaman reference")). In this study, certain odorants were subjected to comparative analysis of the VOCs in order to identify the general trends in the rubber emissions behavior. According to this study, the variation in the identified odors may be associated with specific properties of the rubber, particularly the levels of proteins and the moisture content. By way of example, FIG. 1, which corresponds to FIG. 8 of the Kamarulzaman reference, represents the chemical groups obtained from a heated rubber (see also Table 3 of the Kamarulzaman reference). The dominant group of VOCs released by the heated sample was aromatic compounds, followed by ketones, aldehydes, acids and cyclic-type compounds. The sulfur-containing and nitrogen-containing groups exhibited a low and similar percentage of odorants, although these were still capable of contributing to the olfactory profile.

There are commercially available tools aimed at recognizing the presence of a target compound (for example, a chemical or biological analyte) in a gas sample. Of these tools, electronic noses often employ one or more sensors that measure the concentration of a substance using SPR (Surface Plasmon Resonance) (see "Highly-Selective Optoelectronic Nose Based on Surface Plasmon Resonance Imaging for Sensing Volatile Organic Mixtures", by Sophie Brenet, Aurelian John-Herpin, François-Xavier Gallat, Benjamin Musnier, Arnaud Buhot, Cyril Herrier, Tristan Rousselle, Thierry Livache, and Yanxia Hou, in *Analytical Chemistry*, 90, 9879-9887 (2018)). The SPR technique can measure the interaction between the molecules by using optical principles without a separate marking substance such as a fluorescent material. The surface plasmons are quantified vibrations of free electrons moving along the surface of a conductor, such as a metallic surface. These surface plasmons pass through a dielectric medium such as a prism and enter a metallic film at an angle greater than the critical angle of the dielectric medium. They are excited by the incident light and cause resonance at a certain angle. The angle of incidence at which this resonance occurs (referred to as the "resonance angle") is sensitive to the variations in the refractive index of a material close to the metallic film.

SPR involves a known technique of detecting a local change in optical index (being a refractive index) that characterizes the interaction between the target compound and each sensor of the electronic nose. SPR sensors can analyze the samples quantitatively based on the change in refractive index of the material close to the metallic film (i.e., a sample using the above properties). In the analysis of VOCs, the effectiveness of SPR contributes to the good performance of electronic noses, such as their sensitivity, their selectivity, their performance repeatability and their stability. There are also SPR imaging solutions for detecting VOCs in the gas phase that offer good repeatability and good stability (see the solutions disclosed in publications FR3063543, WO2021/009440, WO2021/053284 and WO2021/053285 and commercially available from Aryballe Technologies).

Furthermore, recent improvements in machine-learning and data-analysis techniques, combined with platforms for computing and storing data, have opened the way to development of new approaches for combining olfactory profiles and solutions using the SPR effect. In the field of artificial intelligence (or "AI"), machine-learning techniques are known, and their essence is to be "trained" on a high number of situations. By virtue of adjustment of weighting coefficients in a training phase, machine learning may predict the result of a new situation presented thereto. It will be noted that a plurality of different machine-learning methods are possible, including supervised learning (in which the algorithm is trained on a set of labelled data and learns until it is capable of obtaining the desired result), unsupervised or semi-supervised learning (in which the data are not labelled so that the network may learn so as to increase the accuracy of the algorithm), reinforcement learning (in which the algorithm is rewarded for positive results and punished for negative results) and active learning (as it learns, the algorithm requests examples and labels to refine its prediction) (see https://www.lebigdata.fr/reseau-de-neurones-artificiels-definition).

When seeking to evaluate the parameters of a rubber product, some of these are not accessible via measurement means. For example, the aging is currently managed through empirical expiry dates. As far as the tack is concerned, the shop floor chiefly makes use of rolling ball tack testers in order to estimate the tack of a product, and this entails taking a sample. In both instances, the measurement is subject to the "operator" effect in addition to the other measurement errors.

Thus, establishing a link between odors and odorous substances can benefit the impact of odors in the manufacture of rubber products and develop effective production and management practices on a rubber product production site. The disclosed invention therefore combines SPR data, obtained by electronic noses, and the rubber-product production facilities in order to benefit from the physicochemical properties known in the field of rubber-product production (for example, characteristic odors that influence the tack of the mixtures on the industrial methods) (as used herein, the terms "mixture" and "rubber mixture" are interchangeable). By using an artificial-intelligence-based system, the data obtained makes it possible to establish a non-obvious connection between the SPR physicochemical aspect and the olfactory aspect of the one or more rubber products in the process of being produced.

SUMMARY OF THE INVENTION

The invention is directed to a method for controlling the manufacture of rubber products produced by a rubber-product manufacturing system including a production facility having at least one mixing means that performs successive steps of mixing a rubber mixture, characterized in that the method comprises the following steps:

a step of initiating a mixing cycle that is performed at the production facility;

a step of capturing ambient air of the production facility in order to obtain at least one gas sample during the mixing cycle, this step being performed by an odor detection device of the system that recognizes the presence of odorous volatile organic compounds present in the ambient air received by the device by measuring its concentration using surface plasmon resonance;

a step of detecting olfactory profiles present in the ambient air and captured by the device;

a step of identifying an olfactory profile in order to identify a mixture leaving the mixing means and the production status thereof, this step being performed on the basis of at least one sample of the ambient air captured by the device;

a step of analyzing the samples captured by the device against one or more SPR imprints supplied by the device and the extracted data represented therein;

a step of constructing at least one olfactory-profiles model from the physicochemical properties of the identified rubber mixture, this step including a step of introducing the physicochemical properties of the identified rubber mixture into a neural network, this step being performed by the system; and a step of training the olfactory-profiles model using the olfactory profiles of the identified rubber mixture;

such that the output olfactory-profiles model will be the identification of the physicochemical properties of the rubber mixture in the process of being produced in the production facility. In some embodiments of the method of the invention, the step of constructing the olfactory-profiles model includes a step of creating a reference of the olfactory profiles sought to be captured in the ambient air by the device.

In some embodiments of the method of the invention, the introduction step of the step of constructing the olfactory-profiles model includes a step of creating a learning database of the physicochemical properties that is introduced into the olfactory-profiles model.

In some embodiments of the method of the invention, the method further includes a comparison step during which the identification of the physicochemical properties of the mixture leaving the mixing means, output from the olfactory-profiles model, is compared against the olfactory profile of the identified mixture so that the system can adjust the production facility in the event that the desired properties for the mixture are not attained. In some embodiments of the method of the invention, the method further includes a step of controlling an adjustment of the production facility to predict the attainment of the desired properties of the mixture exiting the mixing means. In such embodiments of the method of the invention, the step of controlling the adjustment of the production facility includes a step of determining a level of tack of the mixture from an SPR imprint supplied by the device.

In some embodiments of the method of the invention, during the step of training the olfactory-profiles model, the system employs a learning method selected from a machine learning method and a progressive-learning method.

In some embodiments of the method of the invention:

the step of detecting olfactory profiles includes a step of eliminating VOC pollution from the ambient air received by the device, this step being performed by a filter of the system before the ambient air enters the device;

the step of identifying an olfactory profile includes a step of reducing the moisture content and/or the temperature of the ambient air received by the device, this step being performed by a condenser of the system; and the step of analyzing the samples captured by the device further includes a step of analyzing olfactory profiles in the samples prior to the analysis performed by the device, this step being performed by a multiplexer of the system.

In some embodiments of the method of the invention, the step of initiating a mixing cycle includes a step of introducing, into the mixing means, the raw materials needed for performance of the production of the mixture.

In some embodiments of the method of the invention, the starting step of initiating a mixing cycle includes a step of introducing, into the mixing means, one or more master-batches.

In some embodiments of the method of the invention, the method further includes a step of simulating a number of mixing operations yielding at least one rubber mixture having predetermined physicochemical properties.

The invention is also directed to a system for manufacturing rubber products that performs the disclosed methods for controlling the manufacture of rubber products, characterized in that the system includes:

a production facility that implements successive mixing steps, the production facility including at least one mixing means from which one or more rubber mixture(s) exit;

an odor detection device that captures ambient air of the production facility in order to obtain at least one gas sample during the mixing cycle; and a control subsystem that employs an olfactory-profiles model based on physicochemical characteristics of the rubber mixtures recognized by surface plasmon resonance (SPR);

such that the device recognizes the presence of odorous volatile organic compounds (VOCs) present in the captured ambient air by measuring the concentration thereof using surface plasmon resonance (SPR); and such that the olfactory-profiles model learns the physicochemical properties of the VOCs associated with the mixtures exiting the mixing means during the rubber-product production cycles performed by the production facility.

In some embodiments of the system of the invention, the subsystem includes one or more sensors that trigger when the output olfactory-profiles model indicates an offset between the physicochemical properties of the mixture that is in the process of being produced in the production facility and its expected physicochemical properties. In such embodiments of the system of the invention, the subsystem adjusts the operation of the production facility in response to the triggered sensors so as to obtain a level of tack of the mixture from an SPR imprint supplied by the device.

In some embodiments of the system of the invention, the mixing means is selected from one or more extruder(s) and/or one or more internal mixing mill(s).

Further aspects of the invention will become apparent from the following detailed description.

BRIEF DESCRIPTION OF THE DRAWINGS

The nature and various advantages of the invention will become more evident from reading the following detailed description, in conjunction with the appended drawings, in which the same reference numerals denote identical parts throughout, and in which:

FIG. 1 represents a set of chemical groups obtained from a heated rubber.

FIG. 2 represents an embodiment of a system for manufacturing rubber products of the invention.

FIG. 3 represents an embodiment of the system of FIG. 2.

FIG. 4 represents an embodiment of a method for controlling the manufacture of rubber products performed by the system of the invention.

DETAILED DESCRIPTION

With reference now to the figures, in which the same numerals identify identical elements, FIG. 2 shows a system for manufacturing rubber products (or "system") 100 of the invention. The system 100 performs a method for controlling the manufacture of rubber products in response to the input of data obtained by a detection tool enabling a physicochemical classification (also referred to as an "electronic nose") of the system. The system 100 can be used in facilities in which rubber products (including tires) are manufactured. It is understood that the system 100 can operate in numerous physical environments without prior knowledge of their parameters (for example, the initial arrangement of a rubber-product production line of which the system 100 forms a part). The system 100 includes a production facility (or "facility") 110 that implements successive mixing and end-of-line steps. As depicted in FIG. 2, the production facility 110 includes at least one mixing means 112 that performs successive steps of mixing a rubber mixture. By way of example, the mixing means 112 may include at least one extruder 112a having a frame with assembled common parts that may include, without limitation, a screw-barrel assembly (with or without its optional heating and cooling accessories), a drive unit (driving reduction gear and coupling), a main motor, feedstock feed devices (for example, metering devices or hoppers 112b), a control cabinet that groups together the variable speed drives for the motors, start-up and safety devices, and regulating, command, display and measurement devices. The extruder 112a may be a single-screw extruder, a twin-screw extruder, or a multiple-screw extruder.

It is understood that the mixing means 112 may incorporate, in place of the extruder 112a, one or more known internal mixers (not represented) that produce an initial mixture having elastomer materials with carbon black and/or silica as filler. What is meant by an "internal mixing mill" is a machine made up of a ram and two half-tanks (or "tanks"), each containing a rotor with one or more blades (for example, a machine of the Banbury or Intermix type intended for polymers). In another example, the mixing means 112 may incorporate at least one automated external mixer (also referred to as "open mill" or "sheeting mill") into which this worked mixture is then transferred, further circulating it between two rollers so as to transform it into a continuous sheet. Vulcanizing agents (including, but not limited to, sulfur) may be added to the mixture later in a mixing cycle in order to obtain the final mixture for commercial use.

By way of example, the production facility 110 further includes one or more sheeting mills 114 that convert the mixture M leaving the extruder 112a into the form of a strip 115. The strip 115 passes towards one or more sheeting mills 114 that bring it into a continuous form of predetermined width in order to cool the manufactured mixture. It is understood that each sheeting mill may include internal cooling means as known to those skilled in the art. The production facility 110 may include a device for cutting or shaping the extruded material. For example, the continuous strip 115 that is formed may be wound into rolls (represented, by way of example, by the roll 117 in FIG. 2), to facilitate storage of the produced mixture. It is understood that the configuration of the production facility 110 is given by way of example and that other configurations may be incorporated into the system 100. Referring again to FIG. 2, the system 100 also includes an odor detection device (or "device") 120 intended to recognize the presence of a target compound by measuring its concentration using surface plasmon resonance (SPR). The device 120, which receives ambient air from the production facility 110, may include a fan 121 (or equivalent suction device) that draws the ambient air into the device. The flow of ambient air can be regulated by a ventilation means that can selectively retain or discharge the ambient air (for example, a valve that can be selectively opened and closed).

The device 120 also includes one or more sensors 122 that detect the presence of the odorous volatile organic compounds (or "VOCs") present in the ambient air of the production facility 110. The sensors 122 incorporate a sensitive part that interacts with the VOCs (for example, VOCs emitted by the mixture M in the process of being produced in the production facility 110 and represented by the molecules A and B in FIG. 2). Each sensor 122 can detect compounds from a predetermined family of compounds. As understood by a person skilled in the art, this sensitive part may be made of non-biological materials (such as metal oxide semiconductors (or MOS) and polymer semiconductors) or organic molecules (for example, peptides).

The device 120 further includes a thin film, particularly a metallic layer 124, having a surface that remains in contact with the ambient air entering the device. The metallic layer 124 includes a layer of a metal known for producing the SPR effect (for example, gold or silver). The sensors 122 are arranged on this metallic layer 124 in a predetermined layout.

The device 120 also includes a prism 126 having an entry face through which light can enter, an exit face through which light can exit and a support face on which the metallic layer is applied. In one method that creates the SPR effect, an illuminating device 127 of the device 120 emits collimated light through the entry face of the prism 126 until it reaches a surface of the metallic layer 124, this surface exhibiting known reflectivity. The illuminating device 127 may be selected from commercially available illuminating devices, including, without limitation, lights of the LED (light-emitting diode) type.

The illuminating device 127, being sensitive to the refractive index of the ambient air present in the device 120, causes plasmon resonance on the surface of the metallic layer 124. This resonance, being sensitive to the refractive index of the ambient air present in the device 120, reduces the reflectivity of the metallic layer 124 and causes it to vary in the vicinity of each sensor 122. The device 120 may be selected from commercially available odor detection devices (or "electronic noses") (for example, those of the "NeOse" type offered by the company Aryballe, although it is understood that other equivalent devices may be used). The device 120 incorporates at least one processor 128 that is configured to detect the VOCs present in the ambient air and captured by the sensors 122. The term "processor" (or, alternatively, the term "programmable logic circuit") refers to one or more device(s) capable of processing and analyzing data and having one or more software program(s) for the processing thereof (for example, one or more integrated circuit(s) known to a person skilled in the art as being included in a computer, one or more controller(s), one or more microcontroller(s), one or more microcomputer(s), one or more programmable logic controller(s) (or "PLCs"), one or more application-specific integrated circuit(s), one or more neural network(s), and/or one or more other known equivalent programmable circuit(s)). The processor 128 includes one or more software item(s) for processing the volatile compounds captured by the device 120 (and the corresponding data obtained) and one or more software programs for identifying and classifying the olfactory profiles enabling the VOCs to be identified during the course of production of the rubber mixtures. The processor 128 also includes one or more software programs for processing sub-systems associated with the system 100 (and the corresponding data obtained), as well as one or more software programs for identifying variances and for identifying their sources in order to correct them. In order to properly manage the recognition of the odor entering the device 120, it is necessary to identify, in the VOCs present in the ambient air of the production facility 110, the odor that characterizes the rubber product(s) in the process of being manufactured. In particular, identification of olfactory profiles corresponding to the multiple volatile compounds is of relevance to determining correlations between a physicochemical property associated with the rubber (for example, the tack) and the changes in the VOCs originating from the rubber mixtures. Olfactory profiles may be identified in a manner that incorporates the construction of one or more models associated with the SPR chemical aspects and the olfactory aspects of one or more target mixture(s) (also referred to as "the olfactory-profiles model"). An olfactory-profiles model may be used to learn the physicochemical properties associated with the rubber mixtures during the rubber-product production cycles. The term "target compound" (in the singular or in the plural) is used herein to refer to a compound associated with a rubber product (including the mixture M) in the process of being produced in the physical environment of the system 100 and that is identified on the basis of SPR data obtained by the device 120. In order to create a "black box" associated with the rubber mixtures and the olfactory profiles thereof, the parameters pertaining to the various rubber mixtures may be used to form one or more olfactory-profiles models. These data accumulated in the black box may be used to take decisions regarding the control of the parameters of the production facility 110 of the system 100 by examining the odor profiles of the rubber mixtures exiting the facility, the available current odor profiles, the odor profiles of similar mixtures, and/or the time spent detecting the particular VOCs in a mixing cycle. With reference once again to FIG. 2, an embodiment of artificial intelligence may be used by the system 100 to construct at least one olfactory-profiles model. In some embodiments, the processor 128 (alone or in combination with one or more other processor(s)) may configure the system 100 (and notably the device 120) on the basis of one or more physicochemical properties recorded in the olfactory-profiles model. The processor 128 may also refer to a reference in order to make a final determination of the expected physicochemical property or properties. The reference may include at least one reference database incorporating, for example, a table of VOCs of various rubber mixtures (including, without limitation, physicochemical properties corresponding to the VOCs at a specific time during the course of a rubber-mixture mixing cycle). The processor 128 may compare physicochemical properties of the mixture M exiting the mixing means 112 and the olfactory profile of the identified mixture, including the VOCs revealed through the SPR effect, so that the system 100 can adjust the production facility 110 in the event that the desired properties for the mixture M are not attained (for example, by sending an adjustment command to the production facility 110 to predict the attainment of the desired mixture properties). The processor 128 may retrieve from the ambient air captured in the device 120 the physicochemical properties that most closely correspond to the recognized properties for configuring the device. A reference for the ambient air may also include VOC measurements corresponding to a plurality of known olfactory profiles (see, for example, FIG. 1). The data corresponding to the ambient air captured by the device 120 are transferred into and stored in the memory of the processor 128. The processor 128, which executes the instructions of a data processing module of the processor, analyzes the data in order to determine one or more olfactory profiles corresponding to the rubber mixture that is in the process of being produced in the production facility 110. The olfactory profiles are generally indicative of physicochemical characteristics of the mixture that is in the process of being produced. The detection of different chemical groups, such as the VOCs, makes it possible to distinguish along the emissions of the mixture M. The processor 128 can detect changes in the properties of the mixture M in order to identify at least one associated volatile compound. Other features of the mixture M may also be determined.

The captured data may be applied to a determinant of physicochemical properties, including VOCs, that may exploit one or more machine-learning models in order to generate the target compounds. Although the embodiments are described here with regard to the use of neural networks (and more particularly the use of convolutional neural networks (CNNs)) by way of machine learning model, other types of machine learning models may be used. These include, without limitation, models employing linear regression, logistic regression, decision trees, support vector machines, naive Bayes, K-nearest neighbor (kNN), with K signifying a grouping, random forest, dimensionality reduction algorithms, gradient algorithms, neural networks (for example, autoencoding networks, CNNs, RNNs, perceptrons, logarithmic short-term memory (LSTM), Hopfield, Boltzmann, deep belief networks, deconvolution, generative adversarial networks (GANs), etc.) and complements and equivalents thereof. The CNN(s) may be formed using ground truth data that are represented in a VOC reference database created during a method for controlling the manufacture of rubber products, which method is performed by the system 100.

In one embodiment, the system 100 could be optimized using the progressive-learning (or "shaping") principle. Shaping allows new tasks to be learned by reusing characteristics learned during earlier tasks and using characteristics during the course of learning. At a given moment in time, the learned characteristics can be used to perform off-line tasks that may be unsupervised, supervised or semi-supervised. The model, which already has experience of the policy to be adopted when encountering a product of the same type (for example, VOCs attributed to a tacky rubber mixture) learns more quickly than it would if learning from scratch. For the disclosed invention, the training of a neural network, with a view to identifying the primary factors of the SPR that allow estimation of a physicochemical property (for example, the tack, the aging, the pollution, etc.) may entail a vast quantity of data in order to achieve the desired result. It is for that reason that shaping may be chosen to optimize the learning time.

The system 100 of the invention therefore uses the SPR effect to provide one or more digital imprints (or "SPR imprints" or "imprints") of the captured VOCs. By way of example, the imprints EA and EB in FIG. 2 represent the VOCs emitted by the mixture M.

With reference once again to FIG. 2, the system 100 further includes a control subsystem (or "subsystem") 130. The subsystem 130 uses the olfactory-profiles model output by the neural network to control the operation of the production facility 110 in response to the presence of target compounds in the ambient air of the facility. The sensors of the subsystem 130 may trigger when the output olfactory-profiles model indicates an offset between the physicochemical properties of the mixture M in the process of being produced in the production facility 110 (represented by the SPR imprint of the mixture supplied by the device 120) and its expected physicochemical properties. The sensor(s) 122 of the device 120 may detect the presence of the target compounds in the ambient air of the production facility 110, and this triggers the subsystem 130 to change the rotational speed of the screws in the extruder 112a. By way of example, the sensors 122 of the device 120 may detect the presence of target compounds at a level indicating a mixture that is too tacky, enabling modification of the raw materials fed into the extruder 112a. In another example, the detection of ambient air by the device 120 may signal a flow that requires a change of screw (for example, among screws selected from those with interpenetrating co-rotating profiles with conjugated profiles, conjugated or non-conjugated profiles, parallel or conical screws, single-flight or multiple-flight screw profiles, and screws that may or may not be modular).

In some embodiments, the subsystem 130 includes one or more sensors (not represented) that trigger when an image of the production facility 110, together with the output olfactory-profiles model, indicates an offset between the physicochemical properties of the rubber mixture that is in the process of being produced in the production facility 110 and its expected physicochemical properties. In that respect, a sensor of the subsystem 130 may include a camera, photography equipment, an optical sensor and/or other equivalent types of detection equipment.

With reference once again to FIG. 2 and also to FIG. 3, another embodiment of the system 100 is depicted schematically. In this embodiment of the system 100, the system 100 includes the production facility 110 and the device 120 as described hereinabove with reference to the embodiment represented in FIG. 2. The system 100 also includes at least one filter 140 for eliminating VOC pollution from the environment around the production facility 110. The filter 140 can reduce the VOC pollution (for example, with sulfur), thereby allowing the obtention of a stable reference for constructing the olfactory-profiles model. In one embodiment of the filter 140, the filter is an active charcoal filter that is well known in air purification. In order to capture the VOCs from the mixture or mixtures in the process of being produced, the system 100 further includes a gas-concentrating dome 142 that communicates with a condenser 144 of the system 100 (the dome 142 is selected from commercially available domes, for example, of the type offered by the company SoluProTech). The condenser 144, which is selected from among known commercially available condensers, enables reduction of the moisture content and temperature of the ambient air. The system 100 also includes a multiplexer 146 that allows multiple target compounds to be analyzed prior to the SPR analysis performed by the device 120.

In referring still to FIGS. 2 and 3, and also to FIG. 4, a detailed description is given by way of example of a method for controlling the manufacture of rubber products in response to the input of data obtained by the device 120 (or "manufacture control method" or "method") 200 of the invention, which method is performed by the system 100.

At the start of a method for controlling the manufacture of rubber products 200 of the invention, the method includes a step 202 of initiating a mixing cycle in the production facility 110. This step includes an introduction step of introducing, into the mixing means 112, the various raw materials needed for producing rubber products having desired properties (see arrow A in FIG. 2). These raw materials include, without limitation, an elastomer material (for example, a natural rubber, a synthetic elastomer and combinations and equivalents of these) and one or more ingredients such as one or more processing aids, protective agents and reinforcing fillers. The raw materials may also include one or more other ingredients such as carbon black, silica, oils, resins and crosslinking or vulcanization agents (for example, sulfur). All the ingredients are introduced in variable quantities depending on the desired performance of the products obtained by the mixing methods (for example, tires).

The mixing cycle may also be conducted by initiating the cycle using a product that has already been mixed but does not yet contain all of the ingredients in the selected mixture recipe (known as a "masterbatch"). For example, the resins and vulcanization agents are not present in the masterbatch. In this case, either the masterbatch is collected hot from a mixer upstream of the production facility 110 (such as an internal mixer or an external mixer), or the masterbatch is cold because it is being manufactured and packaged several hours or even several days beforehand.

During this step, the mixing means 112 is put into operation (for example, in instances where the mixing means includes the extruder 112a, the screw or screws of the extruder are set in rotation in order to move the rubber mixture towards the downstream end of the extruder as soon as the raw materials are introduced) (see arrow B in FIG. 2). It is understood that the mixing cycle may be easily adapted for all embodiments of the production facility 110 (for example, embodiments involving internal mixers rather than the extruder 112a). During this step, the sheeting mills 114 shape the mixture M exiting the mixing means 112 into a strip 115, and the continuous strip 115 formed is wound into rolls 117 to facilitate the storage of the mixture.

The manufacture control method of the invention also includes a step 204 of capturing ambient air of the production facility 110 in order to obtain one or more gas samples during production of the strip 115. This step, which is performed by the device 120 of the system 100, may be carried out iteratively according to the number of samples intended to be fed into the neural network. The capture step uses an SPR effect employing a local change in refractive index of the rubber mixture produced by the production facility 110. The manufacture control method 200 of the invention further includes a step of detecting olfactory profiles, including VOCs, present in the ambient air and captured by the sensors 122 of the device 120. During this step, these detected olfactory profiles are recorded in one or more database(s) 205. Various parameters, such as the characteristics of the gases (including the nature and concentration of the chemical products, the physicochemical properties of the chemical products, for example, solubility, saturation vapor pressure and biodegradability), the operating conditions and the variations in moisture content of the environment may have an influence on the duration of this step.

In the embodiments of the system 100 that incorporate a filter 140, this step includes a step of removing VOC pollution from the ambient air before it enters the device 120.

The manufacture control method 200 of the invention further includes a step 208 of identifying an olfactory profile so as to identify the rubber mixture that is in the process of being produced and the production status thereof. This step is performed on the basis of at least one sample of the ambient air captured by the device 120. The identification may be made on the basis of the number of samples to be captured. During this step, the extracted data are processed and normalized by the device 120 so that the VOCs can be measured using the SPR effect. The device 120 supplies a imprint of the VOCs present in each sample measured (see, for example, the imprints EA and EB depicted in FIG. 4). This "olfactory" imprint, being an image of the olfactory profile at the instant at which it is measured, varies according to the processing operations performed on the mixture or according to its expected change over the course of a mixing cycle.

In the embodiments of the system 100 that incorporate the condenser 144, this step includes a step of reducing the moisture content and/or the temperature of the ambient air captured by the device 120.

In one embodiment, during the step 208 of identifying an olfactory profile, the device 120 may automatically produce several imprints (for example, during the course of chemical calibration as described in publication FR3063543). The signal representative of the local optical index of a gaseous medium is intentionally variable in order to increase the robustness of the neural network and ensure the acuity thereof.

The manufacture control method 200 of the invention further includes a step 210 of analyzing the samples captured by the device 120. From the imprint supplied by the device 120 and the extracted data represented therein, the extracted characteristics are fed into a VOC classification algorithm on the basis of physicochemical properties. The characteristics mentioned here may include, without limitation, the characteristics of tacky mixtures, the characteristics of de-cohesive mixtures, the addition of water to the mixtures and the aging of the mixtures.

In the embodiments of the system 100 that incorporate the multiplexer 146, this step includes a step of analyzing multiple target compounds in each sample prior to the analysis performed by the device 120.

The manufacture control method 200 of the invention further includes a step of constructing the olfactory-profiles model on the basis of the physicochemical properties of the identified rubber mixture. In order to construct the olfactory-profiles model, this step includes a step 214 of introducing the physicochemical properties of the identified rubber mixture into the neural network, this step being performed by the system 100. During this step, physicochemical properties of the identified rubber mixture are obtained by the device 120. The obtained physicochemical properties include data corresponding to the imprint supplied by the device 120. These data are recorded (for example, in one or more databases 150 of the system 100) (see FIG. 2), and they are updated throughout the duration of the manufacture control method on a continuous or intermittent basis.

The introduction step 214 includes a step of creating a training database (or "database") 215 of the physicochemical properties that is introduced into the olfactory-profiles model. The physicochemical properties correspond to the olfactory profiles of the samples captured by the sensors 122 of the device 120. This step includes a step of creating a reference of the olfactory profiles sought to be captured in the ambient air by the device 120. The reference of the olfactory profiles that is created during this step includes expected olfactory profiles corresponding to the known olfactory profiles of the rubber mixtures in the course of being produced in the production facility 110. This step may be performed in advance of other steps of the method in order to supply the true expected olfactory profiles into the neural network by analyzing the ambient air captured over a number of mixing cycles.

The training database created may include at least one reference database 160 that has been already created (for example, a table of VOCs of various rubber mixtures as discussed above). The database may include parameters corresponding to a plurality of known rubber mixture recipes (including parameters that form part of the general information). In some embodiments of the method 200, at least part of the reference of the olfactory profile is created by one or more person(s) skilled in the art (for example, while recording data captured from the ambient air of other facilities producing a mixture similar to the mixture M exiting the production facility 110).

The manufacture control method 200 of the invention further includes a step 216 of training the olfactory-profiles model. During this step, a machine-learning method receives as input the olfactory profiles obtained from the rubber mixture and the data from the created training database. After the system 100 has obtained the olfactory profiles of the identified rubber mixture, the processor 128 may retrieve its corresponding known physicochemical properties in order to construct the olfactory-profiles model.

In one embodiment, the machine-learning method employed during the training step 216 includes a supervised-learning method. The supervised-learning method may include the training of one or more neural networks as discussed hereinabove.

Thus, the output olfactory-profiles model will be the identification of the physicochemical properties of the rubber mixture in the process of being produced in the production facility 110 (characterized, for example, by the mixture achieving the desired properties at a predetermined time).

This makes it possible, for example, to perform preventive actions in order to ensure that a rubber mixture having the desired properties is attained. By way of example, in certain scenarios, once the training phase is complete, the system 100 can estimate the tack produced from an SPR imprint and other basic data (for example, the temperature and moisture content).

In some embodiments of the manufacture control method 200 of the invention, the method further includes a comparison step 218. During this step, the identification of the physicochemical properties of the mixture M exiting the mixing means 112, output from the olfactory-profiles model, is compared against the olfactory profile of the identified mixture so that the system 100 can adjust the production facility 110 when the desired properties for the mixture M are not attained. In this case, the method 200 further includes a step 220 of controlling adjustment of at least one element of the production facility 110. During this step, an adjustment command is sent to the subsystem 130 to manage the production facility 110 (for example, to trigger the sensors of the subsystem 130 such that the speed of the extruder screws is reduced).

During this step, the system 100 updates the input data (and even the database 221) to support the sharing of information on the physicochemical properties of the rubber mixtures with a production site incorporating the production facility 110 (including operators at the site incorporating the production facility 110). The system 100 implements the method 200 of the invention by using the "stored" VOC measurement data and the "updated" data to prepare customized reminders to be sent to the production facility 110 (or to a site incorporating the production facility 110 or to one or more operators of the site incorporating the production facility 110) and to predict the attainment of desired mixture properties. In this embodiment, the system 100 may propose adjustments to parameters of the mixing cycle in order to improve the rubber mixture exiting the production facility 110.

As used herein, "operator" or "user" refers to a single operator or to a group of operators. An operator includes, without limitation, an individual participant in a task of a mixing cycle performed by the production facility 110, an individual member of a team or of a group that is participating in a mixing cycle, one or more machines associated with an individual or a team that is participating in at least one task of a mixing cycle, a digital community associated with a mixing cycle and combinations and equivalents thereof. The operator may be a spectator watching a mixing cycle, in full or in part, physically or virtually (for example, by remotely managing a live predetermined operation so as to watch the production facility 110 in real time). As used herein, "operator" may also refer to any electronic apparatus or system configured to receive a control input and configured to automatically send data to at least one other operator.

In some embodiments of the method 200 of the invention, the method 200 further includes a step of simulating a number of mixing operations yielding rubber mixtures having predetermined physicochemical properties. Each simulation is then the subject of an olfactory-profile prediction for a rubber mixture having expected physicochemical properties, using an olfactory-profiles model as described hereinabove in order to obtain finally an olfactory-profiles prediction distribution for the identified physicochemical properties. The system 100 of the invention is therefore based on a neural network whose foundation is to be trained on a large number of situations (e.g., ambient air samples) to then be able to describe a new rubber mixture presented to it. On the one hand, one must explain to the neural network what it must recognize, and then make it learn it ("annotation"). On the other hand, the performance of the neural network should be assessed and relevant samples proposed so as to avoid certain biases, such as overtraining, that will reduce the network's performance. Thus, the principle of the system 100 is simply to make what might be considered a difference between the marker elements in the ambient air and the measured. The effects of environmental pollution are mathematically eliminated.

It is conceivable that one or more steps of the method can be performed iteratively.

EXAMPLE

Using reference data (in this instance, the tack and the associated SPR modelling), a neural network that has already had a minimum of training can therefore determine the level of tack as a function of the SPR data. Considering the level of tack in the mixtures in the manufacturing workshops, there are properties of the composition of the mixtures that influence this level of tack, notably:

The ratio of the content of reinforcing filler and the content of plasticizer that indicates a mixture with a higher level of tack when the ratio is lower.

The ratio of resin in the mixture that indicates a mixture with a higher level of tack when the ratio is higher.

The volume fraction of elastomer that indicates a mixture with a higher level of tack when the volume fraction is lower.

Consideration is also given to that characteristic of the elastomer that may influence the level of tack of the mixtures. In this example, what is considered is a Mooney index or Mooney number ML (1+4) 100° C. for dry elastomer <50 points, or the presence of isoprene. The Mooney index, also known by the names of viscosity or plasticity index, characterizes solid substances, as is known. Use is made of an oscillating consistometer as described in standard ASTM D1646 (1999). This plasticity measurement is performed according to the following principle: the sample, analyzed in the raw state (i.e., before curing), is molded (shaped) in a cylindrical chamber heated to a given temperature (for example, 35° C. or 100° C.). After preheating for one minute, the rotor rotates within the test specimen at 2 revolutions/minute, and the working torque for maintaining this movement is measured during 4 minutes of rotation. The Mooney viscosity (ML 1+4) is expressed in "Mooney unit" (MU, with 1 MU=0.83 Nm) and corresponds to the value obtained at the end of the 4 minutes. The term "tack" defines a property of a rubber mixture that varies according to the formulation of the mixture. A mixture with a very high level of tack is not necessarily a mixture that is "at an extreme" in terms of one of the criteria; rather it is the combination of all the criteria that dictates the tack and therefore the difficulty with production. Multiplying these criteria gives a "tack index" which is indicated in the table below:

TABLE 1

| 1-Ratio of Black/Plasticizer | | | | | | | | | | | |
| --- | --- | --- | --- | --- | --- | --- | --- | --- | --- | --- | --- |
| Black/Plasticizer index | 150.38 | 140.30 | 130.23 | 120.15 | 110.08 | 100.00 | 89.92 | 79.85 | 69.77 | 59.70 | 49.62 |
| Severity value | 1 | 1.10 | 1.20 | 1.30 | 1.40 | 1.50 | 1.60 | 1.70 | 1.80 | 1.90 | 2.00 |
| 2-Presence of resin | | | | | | | | | | | |
| Tackifying resin index | 0.00 | 20.00 | 40.00 | 60.00 | 80.00 | 100.00 | 120.00 | 140.00 | 160.00 | 180.00 | 200.00 |
| Severity value | 1 | 1.10 | 1.20 | 1.30 | 1.40 | 1.50 | 1.60 | 1.70 | 1.80 | 1.90 | 2.00 |
| 3-Cohesion of mixture | | | | | | | | | | | |
| Volume fraction of elastomer index | 143 | 134 | 126 | 117 | 109 | 100 | 91 | 83 | 74 | 66 | 57 |
| Severity value | 1 | 1.10 | 1.20 | 1.30 | 1.40 | 1.50 | 1.60 | 1.70 | 1.80 | 1.90 | 2.00 |

Empirically, and according to various industrial feasibility criteria, an assessment of the industrial feasibility of various mixtures is made. The limit of feasibility is established for tack indexes above 3.5 and 4.5 points.

Examples of Mixtures

TABLE 2

| | M tacky | M tacky(a) | M non-tacky |
| --- | --- | --- | --- |
| 1 - Ratio of Black/Plasticizer | | | |
| Black/Plasticizer index | 94.7 | 75.2 | 117.3 |
| Severity value | 1.55 | 1.75 | 1.33 |
| 2 - Presence of resin | | | |
| Tackifying resin index | 132.0 | 112.0 | 20.0 |
| Severity value | 1.66 | 1.56 | 1.10 |
| 3 - Cohesion of mixture | | | |
| Volume fraction of elastomer index | 67.2 | 85.4 | 99.4 |
| Severity value | 1.88 | 1.67 | 1.50 |
| Tack index | 4.9 | 4.5 | 2.2 |

It is absolutely essential to measure the tack of a rubber mixture during the manufacture of certain rubber products. By way of example, for semi-finished products manufactured in the field of tire production, the tack determines the robustness of the assembly of the casing and the cohesion of the products during tire shaping.

Thanks to the system 100 and its use of the SPR effect by the device 120, the disclosed invention is not only highly efficient, but also flexible and adaptable on a case-by-case basis should the need or operating conditions change. The system 100 is therefore suitable for rubber products composed of a variety of rubber mixtures. As a result, the invention takes into account the quality of the parameters measured and analyzed in order to ensure the quality of the rubber products obtained.

It is anticipated that other devices of the electronic nose type may be incorporated into rubber product manufacturing methods. By way of example, an electronic nose employed may use technology based on gas chromatography, based on electrochemical cells (for example, for analyzing target gases such as $NH_3$, $H_2S$, and $CO_2$), based on photoionization detection (PID) and based on interferometry (for example, Mach Zehnder interferometry used in instances in which reduced sensitization to sulfur and other harsh mixtures is desired).

A cycle of the manufacture control method of the invention can be performed under the control of the PLC and may include pre-programming of management information. For example, method regulation may be associated with the desired properties for a mixture produced by the production facility 110, including the properties of the mixing means 112, the properties of the raw materials entering the mixing means and the properties of the mixture exiting the mixing means.

In some embodiments of the invention, the system 100 (and/or a site incorporating the system 100) may receive voice commands or other audio data representing, for example, a command to start or stop capturing samples of the ambient air entering the device 120. The request may include a request for the current status of a mixing cycle performed by the production facility 110. A generated response can be represented audibly, visually, in a tactile manner (for example, by way of a haptic interface) and/or in a virtual and/or augmented manner. For all the embodiments of the system 100, a monitoring system could be installed. At least part of the monitoring system can be supplied in a portable device such as a mobile network device (for example, a mobile telephone, a laptop computer, one or more portable devices connected to the network (including "augmented reality" and/or "virtual reality" devices, wearable clothing connected to the network and/or any combinations and/or any equivalents)).

The system 100 allows continuous measurement of the rubber mixtures originating from the mixing cycles and non-destructive testing that eliminates the operator effect. The system 100 of the invention renders the measurement of the physicochemical characteristics more objective by avoiding rubber sampling by rendering a repeatable measurement.

The terms "at least one" and "one or more" are used interchangeably. The ranges given as lying "between a and b" include the values "a" and "b".

Although particular embodiments of the disclosed apparatus have been illustrated and described, it will be understood that various changes, additions and modifications can be made without departing from either the spirit or the scope of the present description. Therefore, no limitation should be imposed on the scope of the invention described, apart from those disclosed in the appended claims.

The invention claimed is:

1. A method for controlling the manufacture of rubber products produced by a rubber-product manufacturing system comprising a production facility having at least one mixing means that performs successive steps of mixing a rubber mixture, the method comprising the steps:

a step of initiating a mixing cycle that is performed at the production facility;

a step of capturing ambient air of the production facility in order to obtain at least one gas sample during the mixing cycle, this step being performed by an odor detection device of the system that recognizes a presence of odorous volatile organic compounds present in the ambient air received in the odor detection device by measuring a concentration using surface plasmon resonance;

a step of detecting olfactory profiles present in the ambient air and captured by the odor detection device;

a step of identifying an olfactory profile in order to identify a rubber mixture exiting the at least one mixing means and a production status thereof, this step being performed on a basis of at least one sample of ambient air captured by the odor detection device;

a step of analyzing the at least one sample captured by the device against one or more surface plasmon resonance imprints supplied by the odor detection device and extracted data represented therein;

a step of constructing at least one olfactory-profiles model from physicochemical properties of an identified rubber mixture, this step comprising a step of introducing the physicochemical properties of the identified rubber mixture into a neural network, this step being performed by the system; and a step of training the olfactory-profiles model using the olfactory profiles of the identified rubber mixture, wherein an output olfactory-profiles model identifies physicochemical properties of a rubber mixture in a process of being produced in the production facility.

2. The method of claim 1, wherein the step of constructing at least one olfactory-profiles model comprises a step of creating a reference of the olfactory profiles sought to be captured in the ambient air by the odor detection device.

3. The method of claim 2, wherein the introducing step of the step of constructing at least one olfactory-profiles model comprises a step of creating a learning database of the physicochemical properties that is introduced into the olfactory-profiles model.

4. The method of claim 1, further comprising a comparison step during which the identification of the physicochemical properties of the rubber mixture exiting the at least one mixing means, output from the olfactory-profiles model, is compared against an olfactory profile of the identified rubber mixture so that the system can adjust the production facility when desired properties for the rubber mixture are not attained.

5. The method of claim 4, further comprising a step of controlling the adjustment of the production facility such that the rubber mixture exiting the at least one mixing means attains the desired properties.

6. The method of claim 5, wherein the step of controlling the adjustment of the production facility comprises a step of determining a level of tack of the rubber mixture from a surface plasmon resonance imprint supplied by the odor detection device.

7. The method of claim 1, wherein, during the step of training the olfactory-profiles model, the system employs a learning method selected from a machine learning method and a progressive-learning method.

8. The method of claim 1, wherein the step of detecting olfactory profiles comprises a step of eliminating volatile organic compound pollution from the ambient air received by the odor detection device, this step performed by a filter of the system before the ambient air enters the odor detection device, the step of identifying an olfactory profile comprises a step of reducing a moisture content and/or a temperature of the ambient air received by the odor detection device, this step performed by a condenser of the system, and the step of analyzing the at least one sample captured by the odor detection device further comprises a step of analyzing olfactory profiles in the at least one sample prior to the analysis performed by the odor detection device, this step performed by a multiplexer of the system.

9. The method of claim 1, wherein the step of initiating a mixing cycle comprises a step of introducing, into the at least one mixing means, raw materials needed for performing the production of the rubber mixture.

10. The method of claim 1, wherein the step of initiating a mixing cycle comprises a step of introducing, into the at least one mixing means, one or more masterbatches.

11. The method of claim 1, further comprising a step of simulating a number of mixing operations yielding at least one rubber mixture having predetermined physicochemical properties.

12. A system for manufacturing rubber products that performs a method for controlling a manufacture of rubber products, the system comprising:

a production facility that performs successive mixing steps, the production facility comprising at least one mixing means from which one or more rubber mixtures exit;

an odor detection device that captures ambient air of the production facility in order to obtain at least one gas sample during a mixing cycle; and a control subsystem that employs an olfactory-profiles model based on physicochemical properties of rubber mixtures recognized by surface plasmon resonance, wherein the odor detection device recognizes a presence of odorous volatile organic compounds present in the captured ambient air by measuring a concentration thereof using surface plasmon resonance, and wherein the olfactory-profiles model learns physicochemical properties of the volatile organic compounds associated with the one or more rubber mixtures exiting the at least one mixing means during rubber-product production cycles performed by the production facility.

13. The system of claim 12, wherein the control subsystem comprises one or more sensors triggered when an output olfactory-profiles model indicates an offset between the physicochemical properties of the rubber mixture that is in the process of being produced in the production facility and expected physicochemical properties.

14. The system of claim 13, wherein the control subsystem adjusts an operation of the production facility in response to the triggered sensors so as to obtain a level of tack of the rubber mixture from a surface plasmon resonance imprint supplied by the odor detection device.

15. The system of claim 12, wherein the at least one mixing means is selected from one or more extruders and/or one or more internal mixing mills.

* * * * *